United States Patent
Chiba et al.

(10) Patent No.: US 10,390,703 B2
(45) Date of Patent: Aug. 27, 2019

(54) INFORMATION NOTIFICATION SYSTEM, INFORMATION NOTIFICATION METHOD, AND DISPLAY APPARATUS

(71) Applicant: SEIKO EPSON CORPORATION, Tokyo (JP)

(72) Inventors: Shigeto Chiba, Shiojiri (JP); Tsubasa Shirai, Shiojiri (JP)

(73) Assignee: SEIKO EPSON CORPORATION, Tokyo (JP)

(*) Notice: Subject to any disclaimer, the term of this patent is extended or adjusted under 35 U.S.C. 154(b) by 170 days.

(21) Appl. No.: 15/464,721

(22) Filed: Mar. 21, 2017

(65) Prior Publication Data
US 2017/0282040 A1    Oct. 5, 2017

(30) Foreign Application Priority Data
Mar. 29, 2016    (JP) ................. 2016-065212

(51) Int. Cl.
| | |
|---|---|
| *G01C 21/20* | (2006.01) |
| *A61B 5/00* | (2006.01) |
| *A61B 5/11* | (2006.01) |
| *G01S 19/19* | (2010.01) |
| *G01S 19/49* | (2010.01) |
| *G01S 5/00* | (2006.01) |
| *G16H 40/67* | (2018.01) |

(52) U.S. Cl.
CPC .......... *A61B 5/0022* (2013.01); *A61B 5/1112* (2013.01); *A61B 5/6802* (2013.01); *G01S 5/0027* (2013.01); *G01S 19/19* (2013.01); *G01S 19/49* (2013.01); *G16H 40/67* (2018.01); *A61B 2503/10* (2013.01); *A61B 2505/09* (2013.01)

(58) Field of Classification Search
CPC ...... G01C 21/20; G06F 19/3418; G06F 17/30
See application file for complete search history.

(56) References Cited

U.S. PATENT DOCUMENTS

| | | | |
|---|---|---|---|
| 6,266,623 B1* | 7/2001 | Vock ............... | A42B 3/0433 702/41 |
| 9,963,199 B2* | 5/2018 | Hancock .......... | G01S 19/19 |
| 2008/0115050 A1* | 5/2008 | Oliver ............. | G01C 21/20 715/210 |
| 2010/0184563 A1* | 7/2010 | Molyneux ........ | A43B 1/0054 482/1 |
| 2016/0335913 A1* | 11/2016 | Grant .............. | G01S 19/49 |

FOREIGN PATENT DOCUMENTS

| | | |
|---|---|---|
| JP | H06-319842 A | 11/1994 |
| JP | 2013-041360 A | 2/2013 |

* cited by examiner

*Primary Examiner* — Reginald A Renwick
(74) *Attorney, Agent, or Firm* — Oliff PLC

(57) ABSTRACT

A system includes an acquisition section that acquires information from a sensor section attached to each player who is practicing an action in a target area, a processing section that generates area situation information on smoothness of movement of the players in the area based on the information from the sensor sections, and a display apparatus that notifies the area situation information.

24 Claims, 10 Drawing Sheets

INFORMATION NOTIFICATION SYSTEM, INFORMATION NOTIFICATION METHOD, AND DISPLAY APPARATUS

BACKGROUND

1. Technical Field

The present invention relates to an information notification system, an information notification method, and a display apparatus.

2. Related Art

On a skiing ground where skiing, snowboarding, and other sports are practiced, a plurality of sliding action courses of different types are provided, and a player can enjoy a sliding action on a course suitable for the player's skill. In recent years, winter sports in which a person practices a sliding action on a snow surface undergo diversification into fun skiing, telemark skiing, snowboarding, ski-bockerl, airboarding, and the like. Further, an increasing number of people visit distant skiing grounds for good-quality snow.

JPA-6-319842 discloses an apparatus having the function of displaying a congestion situation on a skiing ground, such as a course congested with players, to allow a player to recognize the congestion in advance and select a course where the player desires to practice a sliding action.

The apparatus described in JP-A-6-319842, however, displays the congestion situation in the form of the density of players on a course, and only the information on the displayed congestion situation does not always allow a player to practice skiing, snowboarding, or any other winter sport (hereinafter referred to as skiing as representative example) in a comfortable manner. For example, a player who relies on the displayed congestion situation and arrives at a relatively vacant course cannot practice a sliding sport as intended in some cases if there are other players who are standing still on the course or there are many players who have fallen to the ground. On the other hand, even when a course on which a player is intended to practice a sliding action is relatively congested with other players, but the other players on the course are practicing sliding sports at speeds similar to the speed of the player, the player can practice the sliding sport as intended in some cases.

SUMMARY

An advantage of some aspects of the invention is to provide a system and the like that assist a player who practices a sport, such as skiing, in practicing the sport more comfortably than ever.

APPLICATION EXAMPLE 1

An information notification system according to this application example includes an acquisition section that acquires information from a sensor attached to each player who is practicing an action in a target area, a processing section that generates area situation information on smoothness of movement of the players in the area based on the information from the sensors, and a notification section that notifies the area situation information.

According to this application example, since the notified area situation information contains information on the smoothness of the movement of the players, each of the players who, for example, practices skiing, can use the area situation information as a reference for identifying an area suitable for the player's sliding action skill and sliding action method. Since the information on the smoothness of the players' movement that cannot be identified by methods of related art is provided, a system that assists players who practice sports, such as skiing, in such a way that the players practice the sports more comfortably than ever can be provided.

APPLICATION EXAMPLE 2

The area situation information described in the above application example may contain information on moving speeds of the players in the area.

According to this application example, the information on the players' moving speeds can be used as an index of the smoothness of the players' movement.

APPLICATION EXAMPLE 3

The area situation information described in the above application example may be screen information containing positions of the players or density of the players and the moving speeds displayed on a map of the area.

According to this application example, the screen information displayed on the map can visually convey the smoothness of the movement of the players in the area to the players.

APPLICATION EXAMPLE 4

The area may be formed of a plurality of areas, and the area situation information described in the above application example may be screen information containing the density and the moving speeds diagrammatically expressed in each of the plurality of areas.

According to this application example, the diagrammatically expressed screen information can visually convey characteristics of the density and speeds representing the smoothness of the movement of the players in the area to the players.

APPLICATION EXAMPLE 5

The processing section described in the above application example may use the information from the sensors to calculate trajectories along which the players practice the actions in the area and a width of an area where the players are allowed to practice the action.

According to this application example, the area situation information can be generated on the basis of the trajectories along which the players practice the actions and the area where the players are allowed to practice the actions.

APPLICATION EXAMPLE 6

The processing section described in the above application example may calculate the density of the players in the area based on the positions and the trajectories of the players in the area and the width in the area.

According to this application example, the density of the players in the area where the players are allowed to practice the actions can be calculated. For example, even when the range of the action practicable area changes due to the conditions of the area, the density of the players in the area where the players can actually practice the actions can be calculated in correspondence with the change.

APPLICATION EXAMPLE 7

The area situation information described in the above application example may be screen information containing the density displayed on a map of the area.

According to this application example, the density of the players in an actual action practicable area can be visually conveyed to the players.

APPLICATION EXAMPLE 8

The processing section described in the above application example may generate going-off-course information when any of the players moves out of the area, and the notification section may notify the going-off -course information.

According to this application example, a player who has moved out of the area can be notified that the player has moved out of the area.

APPLICATION EXAMPLE 9

Each of the sensors described in the above application example preferably includes a positioning sensor.

APPLICATION EXAMPLE 10

The notification section described in the above application example may include at least one of a display apparatus attached to each of the players, a display apparatus installed in the area, and a display apparatus provided in a server that acquires the information from the sensors.

According to this application example, the notification can be performed by using a wide variety of display apparatus.

APPLICATION EXAMPLE 11

An information notification method according to this application example includes acquiring information from a sensor attached to each player who is practicing an action in a target area, generating area situation information on smoothness of movement of the players in the area based on the information from the sensors, and notifying the area situation information.

According to this application example, since the notified area situation information contains information on the smoothness of the movement of the players, each of the players who, for example, practices skiing, can use the area situation information as a reference for identifying an area suitable for the player's sliding action skill and sliding action method. Since the information on the smoothness of the players' movement that cannot be identified by methods of related art is provided, a method that assists players who practice sports, such as skiing, in such a way that the players practice the sports more comfortably than ever can be provided.

APPLICATION EXAMPLE 12

A program according to this application example causes a computer to acquire information from a sensor attached to each player who is practicing an action in a target area, generate area situation information on smoothness of movement of the players in the area based on the information from the sensors, and notify the area situation information.

According to this application example, since the notified area situation information contains information on the smoothness of the movement of the players, each of the players who, for example, practices skiing, can use the area situation information as a reference for identifying an area suitable for the player's sliding action skill and sliding action method. Since the information on the smoothness of the players' movement that cannot be identified by methods of related art is provided, a program that assists players who practice sports, such as skiing, in such a way that the players practice the sports more comfortably than ever can be provided.

BRIEF DESCRIPTION OF THE DRAWINGS

The invention will be described with reference to the accompanying drawings, wherein like numbers reference like elements

DESCRIPTION OF EXEMPLARY EMBODIMENTS

Embodiments of the invention will be described below with reference to the drawings. In the following drawings, each screen and each portion are so drawn at scales different from actual scales as to be large enough to be recognizable. Further, the embodiments are described with reference to a case where skiing presented as an example of winter sports. The invention is also applicable not only to skiing but also to other winter sports and other outdoor sport, indoor sports, and other sports. These cases will be described later with reference to variations.

First Embodiment
Overview of Information Notification System

Figure 1:
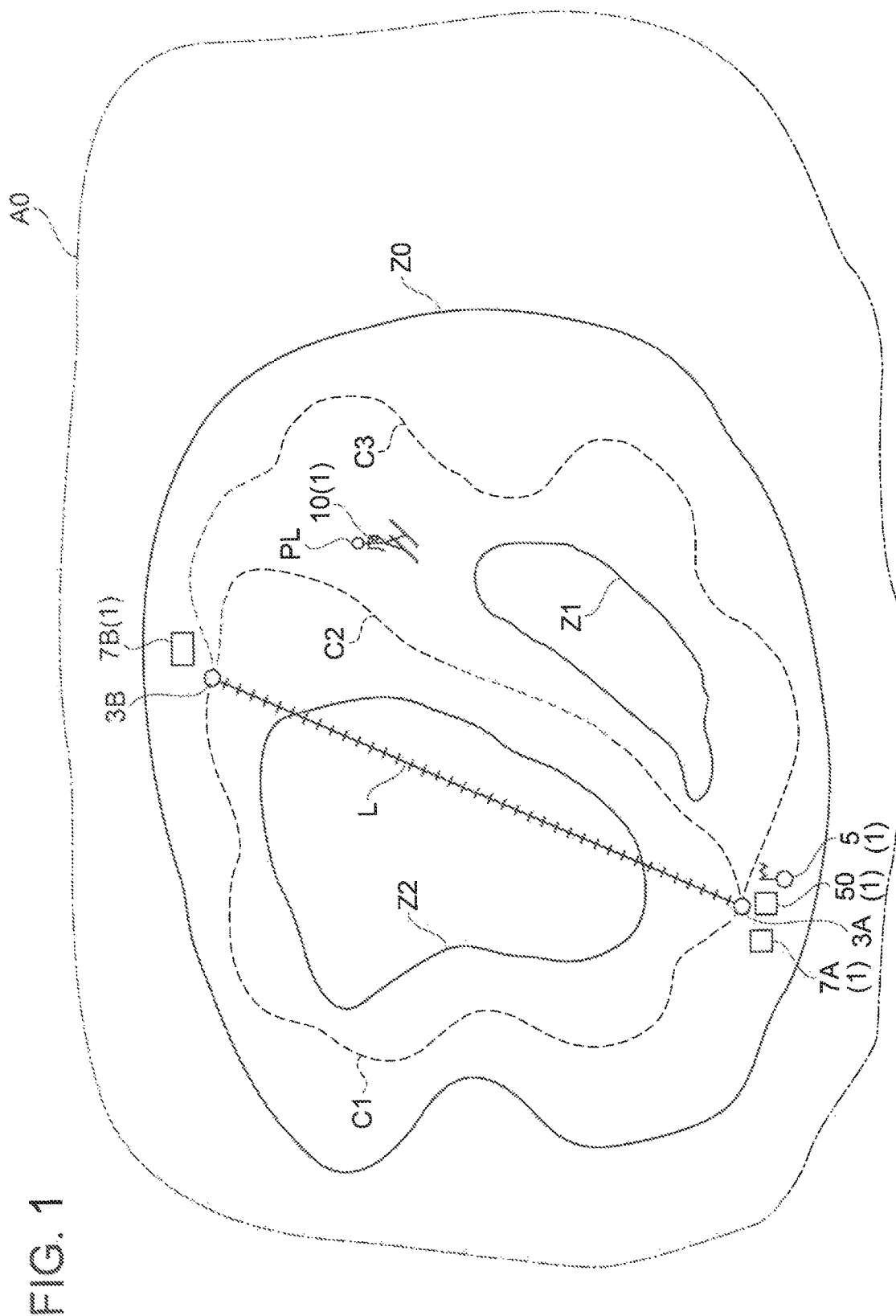
FIG. 1 is a descriptive diagram showing an environment where an information notification system is used.
Figure 2:
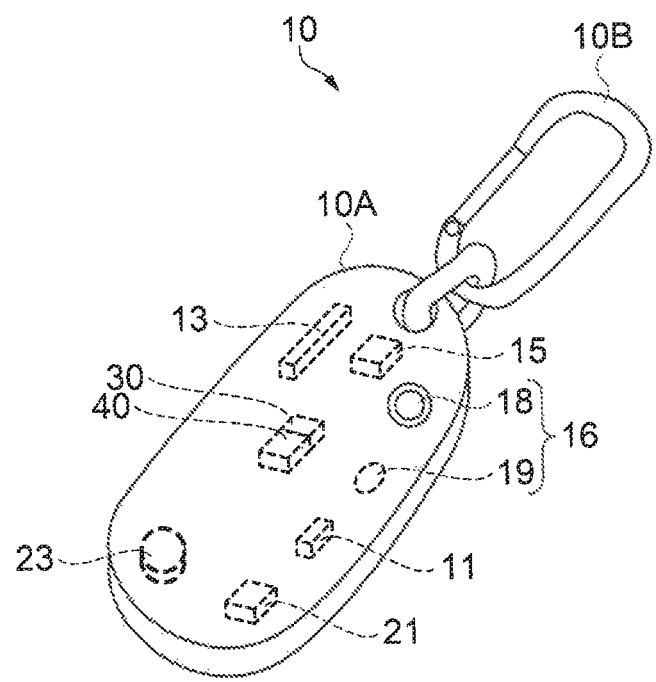
FIG. 2 is a descriptive diagram showing an overview of an attachment device.
Figure 3:
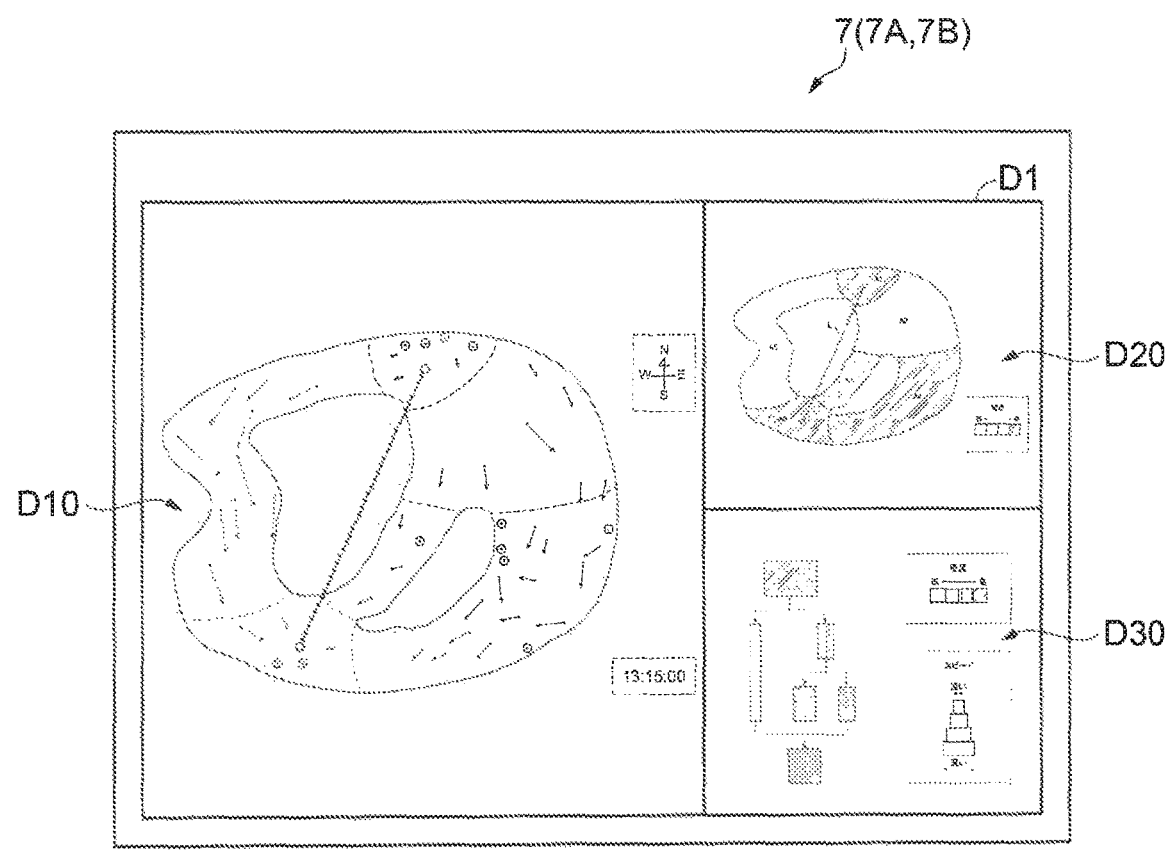
FIG. 3 is a descriptive diagram showing a display screen of a display apparatus.

FIG. 1 is a descriptive diagram showing an environment where an information notification system is used. FIG. 2 is a descriptive diagram showing an overview of an attachment device. FIG. 3 is a descriptive diagram showing display screens of a display apparatus.

The descriptive diagram shown in FIG. 1 conceptually shows a skiing ground viewed from above. An information notification system 1 is a system having components installed at a variety of points on the skiing ground, which is the environment where the information notification system 1 is used.

The skiing ground will first be described with reference to FIG. 1. A region A0 is a region representing the entire site of the skiing ground. The region within a region ZO but outside regions Z1 and Z2 is a slope where a player PL can practice a sliding action. The action of the player PL who skis is referred to as a sliding action. The regions within the regions Z1 and Z2 and the region outside the region Z0 are regions where no sliding action is allowed. On the slope where players are allowed to practice sliding actions, a course C1, a course C2, and a course C3 are formed as sliding action courses. The player PL who is practicing a sliding action is conceptually shown between the courses C2 and C3. An attachment device 10 is attached to the player PL. The wire of a lift. L is so installed in a central portion of the region Z0 as to traverse over the region Z2. The lift L carries the player PL from a lift gate 3A to a lift gate 3B along the wire. The lift gate 3B is located in a position higher than the lift gate 3A in terms of altitude. The lift gate 3A has the function of automatically examining a lift ticket. Each of the regions A0, Z0, Z1, and Z2 corresponds to the area set forth in the appended claims.

The information notification system 1 includes the attachment device 10, a server 50, display apparatus 7A and 7B, a communication antenna 5, and other components. The attachment device 10 is attached to the player PL. The server 50, the display apparatus 7A, and the communication antenna 5 are installed in a building in which the lift gate 3A is located or in a space outside the building. The display apparatus 7B is installed in the vicinity of the lift gate 3B.

The attachment device 10 shown in FIG. 2 is a device attached to or carried by the player PL, and a compact thin. (for example, 5 mm in thickness and about 3 to 5 cm in longitudinal direction) enclosure 10A is provided with a hook 10B, which can be attached to the clothes, an outfit, or any other object of the player PL. Without use of the hook 10B, the attachment device 10 may instead be accommodated in a ticket holder or a pocket on an upper arm of the player PL. The enclosure 10A accommodates a noncontact communication section 11, a positioning sensor 13, an acceleration sensor 15, an LED 18, a buzzer 19, a communication section 21, a power supply 23, a control section 30, a memory section 40, and other components. Each of the constituent portions described above will be described later in detail. A primary function of the information notification system 1 will be described below with reference to part of the constituent portions.

The attachment device 10 is a constituent portion of the information notification system 1 and is also a device that can be used as a replacement for a lift ticket. When the player PL purchases a lift ticket, which is a ticket that allows the player PL to ride the lift, the attachment device 10 instead of the lift ticket is lent the player PL. That is, each player who uses the lift L wears the attachment device 10.

The noncontact communication section 11 is a noncontact IC chip, wirelessly communicates with the automatic ticket examiner of the lift gate 3A in a noncontact manner, and transmits lift ticket purchase certification. The positioning sensor 13 and the acceleration sensor 15 measure sensor information, such as the position, moving speed, and moving direction of the player PL, and the communication section 21 transmits the measured sensor information toward the communication antenna 5.

The server 50 is so connected to the communication antenna 5 and the display apparatus 7A and 7B as to he capable of data communication. The server 50 collects sensor information transmitted from the attachment devices 10 on all players and received with the communication antenna 5. The server 50 generates a screen D1 (FIG. 3) on the basis of the collected sensor information and transmits the screen D1 to the display apparatus 7A and 7B. Each of the display apparatus 7A and 7B is a large-screen (for example, at least 50-inch) display apparatus and is visually recognized by a large number of players. The screen D1 displayed on the display apparatus 7A and 7B is formed of screens D10, D20, and D30.

The screen D10 is a screen referred to as an analysis map screen and visually conveys information on the position, moving speed, and moving direction of each player to whom the attachment device 10 is attached. The screen D20 is a screen referred to as a density map screen and visually conveys information on the density of the players in each of regions into which the area Z0 is divided on the basis of sliding action situations and other factors. The screen D30 is a screen referred to as an analysis graph screen and visually conveys analyzed characteristics, such as the density and moving speeds of the players in each of the regions divided in the screen D20, in the form of graphs. The screens D10, D20, and D30 will be described later in detail with reference to FIGS. 5, 6, and 7, respectively.

The player PL, to whom the attachment device 10 is attached, trans its the sensor information, which is information provided from the sensors and measured when the player PL practices a sliding action, to the server 50 and visually recognizes the screen D1 generated on the basis of the sensor information similarly collected from other players and displayed on the display apparatus 7A and 7B. The players positions, moving speeds, and moving directions, the analyzed characteristic of the density and moving speeds, and other factors displayed on the screen D1 are used as indices representing the degree of smoothness of the players' movement. The player PL visually recognizes the screen D1 and is therefore capable of selecting a course and a region suitable for the playstyle of the player PL and practicing a sliding action.

In the following sections, the configuration of the information notification system 1 capable of providing the advantageous effect described above will be described, below in detail.

Configuration of Information Notification System

Figure 4:
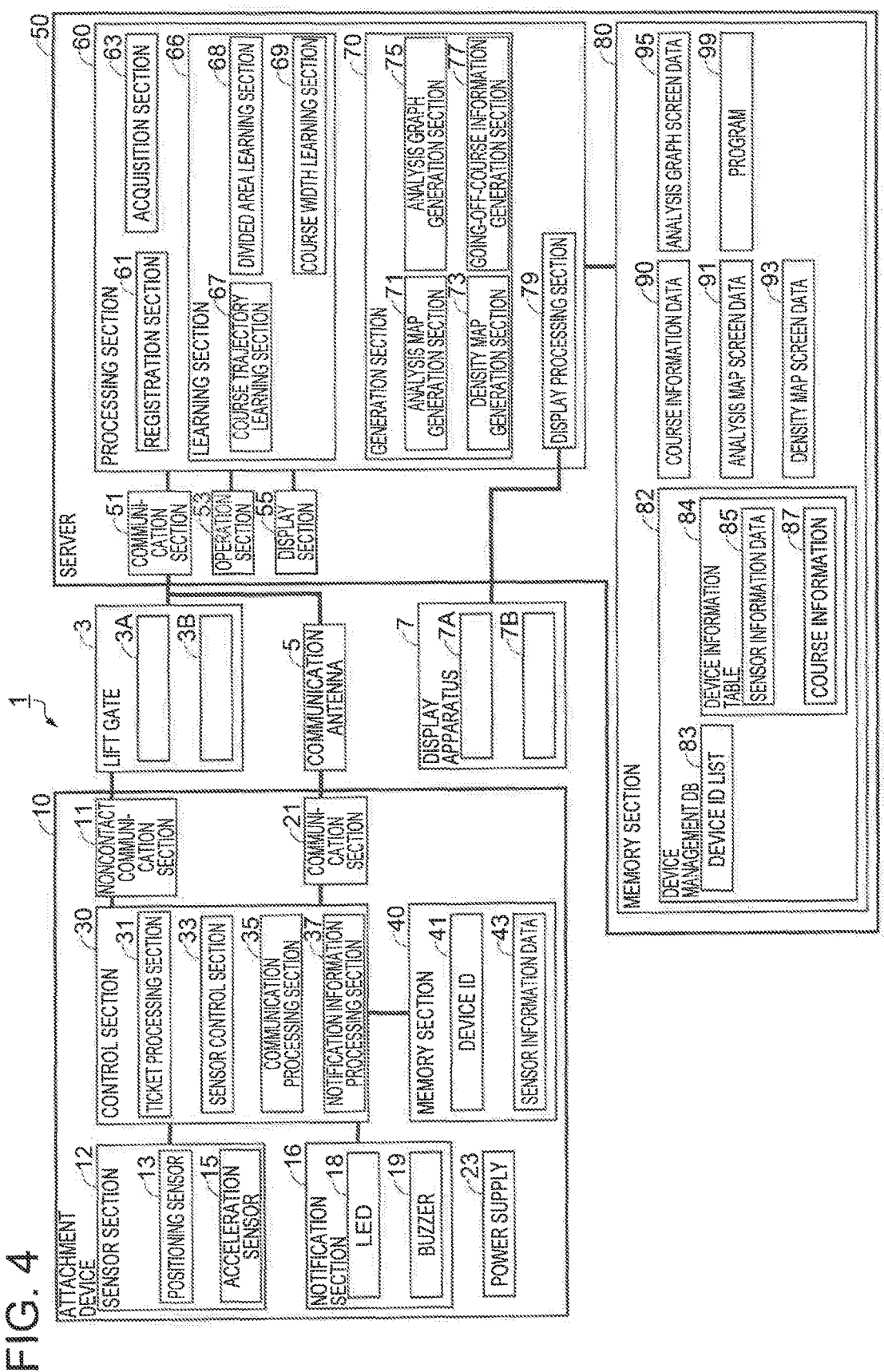
FIG. 4 is a block diagram showing a schematic configuration of the information notification system.

FIG. 4 is a block diagram showing a schematic configuration of the information notification system. The information notification system 1 includes the lift gates 3, the communication antenna 5, the display apparatus 7, the attachment devices 10, and the server 50, The lift gates 3 include the lift gate 3A and the lift gate 3B described above. The number of lift gates 3 may be increased in accordance with the number of lifts L constructed on the skiing ground.

The lift gate 3A has the automatic ticket examining function, as described above. Specifically, the lift gate 3A has a wireless transceiver and receives a ticket number corresponding to lift ticket purchase certification when the noncontact communication section 11 of any of the attachment devices 10 approaches the lift gate 3A. The lift gate 3A is so connected to the server 50 as to be capable of data communication and has received information related to the ticket number in advance. Specifically, the lift gate 3A has received information on whether or not the ticket number is valid (whether or not lift ticket has been purchased), a valid timeframe, and other factors. When the ticket number received from the attachment device 10 is valid, the lift gate 3A opens the gate to guide the player to the lift boarding point, whereas when the ticket number is invalid, the lift gate 3A does not open the gate. The lift gate 3A transmits information on the acquired ticket number, a result of the gate operation or whether or not the gate was opened, the time when the ticket number was examined, and other pieces of information to the server 50.

The communication antenna 5 is an antenna capable of transmitting and receiving a wireless signal to and from the attachment devices 10. The communication antenna 5 only needs to be capable of communication over a range that covers at least the area A0 and may use, as a communication method, for example, mobile phone communication, such as 3G and 4G, high-speed data-only communication that covers a middle/long range, such as WiMAX (registered trademark), or wireless LAN communication, such as WiFi (registered trademark). The communication antenna 5 may be formed of a plurality of communication antennas 5 installed over a range that covers the area A0. The communication antenna 5 is connected to a communication section 51 of the server 50, and a variety of wireless signals transmitted from the communication antenna 5 and received, by the server 50 are converted into a variety of data handled by the server 50 under the control of the server 50.

The display apparatus 7 includes the display apparatus 7A and 7B described above. Each of the display apparatus 7A and 7B is, for example, a large liquid crystal display apparatus or a projector that performs projection on a large screen. The number of display apparatus 7 is not limited to two and may instead be one or three or more. The display apparatus 7 (display apparatus 7A and 7B) correspond to the display apparatus installed in the area and the notification section set forth in the appended claims.

Configuration of Attachment Device

Each of the attachment devices 10 includes the noncontact communication section 11, a sensor section 12, a notification section 16, the communication section 21, the power supply 23, the control section 30, and the memory section 40.

The noncontact communication section 11, which is the noncontact IC chip described above, communicates with the wireless transceiver provided in the automatic ticket examiner of the lift gate 3A and transmits information on a ticket number, which serves as lift ticket purchase certification information. The ticket number is stored in the attachment device 10 lent to a player when the player purchases a lift ticket. The noncontact IC chip may be replaced with an IC tag or an RF (radio frequency) tag. A ticket number is written onto the IC tag or the RF tag, which is attached to the attachment device 10 when a lift ticket is purchased. Also in this case, the ticket number is managed in the server 50 and transmitted to the lift gate 3A in advance.

The sensor section 12 includes the positioning sensor 13, the acceleration sensor 15, and other sensors.

The positioning sensor 13 includes a positioning antenna (not shown) and is intended to calculate information on the position of the attachment device 10 by using satellite signals transmitted from GNSS (global navigation satellite system) satellites. The positioning antenna is an antenna that receives an RF (radio frequency) signal including a satellite signal transmitted from a GNSS satellite. The received RF signal is outputted to the positioning sensor. In the present embodiment, the description will be made of a case where GPS (global positioning system) is used as GNSS.

The positioning sensor 13 is formed of an LSI (large scale integration) element including an RF receiving circuit and a baseband module and extracts and acquires positioning-related information superimposed on the RF signal inputted via the positioning antenna. In detail, signal processing is performed on the inputted RF signal to capture a satellite signal from a GPS satellite. A navigation message superimposed on the captured satellite signal is separated, and positioning information contained in the navigation message is acquired. The positioning information contains an almanac and an ephemeris. The received satellite signal also contains information on correct transmission time when the satellite signal is transmitted from the GPS satellite and information on electric-wave propagation delay at the time of reception of the satellite signal, and a pseudo distance between the GPS satellite and the attachment device 10 is calculated. The pseudo distance and the information on almanac and ephemeris are acquired at least from four GPS satellites, and a known position calculation process is carried out to calculate the position (positional coordinates) and a timepiece error (clock bias) of the attachment device 10. The position calculation process can be achieved, for example, as a process to which a least square method, a Kalman filter, or any other approach is applied. The calculated position information is outputted to the control section 30.

The positioning sensor 13 can instead calculate the position information on the basis of the reception frequency of the received signal acquired from each of the GPS satellites. In this method, a known position calculation operation is performed on the basis of a code phase or any other factor from each of at least four GPS satellites to calculate, as the positional coordinates, a vector quantity having components in three directions perpendicular to one another. Still instead, a known operation is performed on the basis of frequency or any other factor received from each of at least four GPS satellites (such as Doppler frequency determined from received frequency) to calculate, as a velocity vector, a vector quantity having components in three directions perpendicular to one another and determine the moving direction and the moving speed of the attachment device 10. The positioning sensor 13 outputs the thus calculated sensor information containing the position, moving speed, and moving direction of the attachment device 10 and the time when the positioning is performed to the control section 30.

The acceleration sensor 15 is a known MEMS sensor that detects acceleration in three axial directions roughly perpendicular to one another, calculates information, such as the inclination and travel of the attachment device 10, from an acceleration signal detected on a fixed period (ranging from about 15.6 to 62.5 msec, for example) basis, and outputs the calculated information as the sensor information to the control section 30. The information on the inclination and travel is used to calculate the position, moving speed, and moving direction of the attachment device 10 in a timeframe for which no sensor information is outputted from the positioning sensor 13 (such as in indoor environment). The information on the inclination and travel of the attachment device 10 may also be used to interpolate information in the gap between two points of time when the information on the position, moving speed, and moving direction is outputted from the positioning sensor 13. Further, the information on the inclination and travel of the attachment device 10 may be transmitted to the server 50 and used by the server 50 as information n the player's action.

The sensor section 12 corresponds to the sensor set forth in the appended claims, and the sensor information corresponds to the information from the sensor set forth in the appended claims.

The notification section 16 includes the LED 18 and the buzzer 19. The LED 18 is a light emitting element, such as an LED (light emitting diode), and the buzzer 19 is formed, for example, of a loudspeaker or a piezoelectric vibrator. Each of the LED 18 and the buzzer 19 performs a variety of types of notification on the basis of a notification signal inputted from the control section 30. The notification section 16 corresponds to a notification section set forth in the appended claims.

The communication section 21, which is a wireless communication adaptor, transmits and receives a wireless signal via the communication antenna 5 and transmits and receives a variety of data to and from the server 50. The communication section 21 uses the same wireless signal communication method used by the communication antenna 5 and uses the same communication protocol used by the server 50. The wireless signal complies, for example, with mobile phone communication, WiMAX, car WiFi, and the communication protocol is, for example, IP (Internet Protocol). It is noted that the configuration described above is not necessarily employed and the communication section 21 only needs to be a communication adaptor capable of wirelessly communicating with the communication antenna 5 and the server 50.

The power supply 23 is a power supply that supplies each section of the attachment device 10, such as the sensor section 12, the notification section 16, and the control section 30, with electric power and is formed, for example, of a secondary battery or a charging circuit. The secondary battery is, for example, a nickel-hydrogen battery or a lithium ion secondary battery. The charging circuit may be a circuit that converts electric power supplied from an AC power supply or any other power supply into DC electric power and charges a target with the DC electric power or a charging circuit that performs solar power generation (solar cell) that generates and supplies electric power, vibration-based power generation, hand winding power generation, or any other types of power generation. The power supply 23 is not limited to a secondary battery and may instead be a primary battery having a button shape, a coin shape, a sheet shape, or any other shape.

The control section 30 is not only a control device but also a computation device that synthetically control each portion of the attachment device 10 in accordance with a variety of programs (not shown) memorized in the memory section 40 and includes a CPU (central processing unit), a DSP (digital signal processor), or any other processor.

The control section 30 executes the programs memorized in the memory section 40 to achieve the function of each of the following functional sections: a ticket processing section 31; a sensor control section 33; a communication processing section and a notification information processing section 37. It is, however, noted that the functional sections described above are presented only by way of example and all the functional sections are not necessarily provided as essential components. Further, another functional section in addition thereto may be added as an essential component.

The ticket processing section 31 carries out a lift ticket purchase process. The ticket processing section 31 is a functional section activated when a player purchases a lift ticket and functions in synchronization with a registration section 61 in the server 50. The timing when a player purchases a lift ticket is also the timing when the attachment device 10 is given (lent) to the player for the first time. When the function of the functional section is performed, the player to whom the attachment device 10 is attached is allowed to pass through the automatic ticket examiner of the lift gate 3A.

As a specific process, the ticket processing section 31 memorizes the ticket number in the Memory section 40 and in the IC chip in the noncontact communication section 11. The ticket number is a number issued by the server 50 as the purchase certification that certifies purchase of a lift ticket. When issued, the ticket number is registered in the server 50 and transmitted to the lift gate 3A. The ticket number may also serve, for example, as a device ID 41 (memory section 40), which is an identifier assigned to each attachment device 10. When the player finishes skiing and returns the attachment device 10, the ticket number is deleted or invalidated in the server 50, and the ticket number stored in the attachment device 10 is also deleted or processed as invalid information.

In the case where the noncontact communication section 11 is an IC tag or an RF tag, the ticket number written onto the IC tag or the RF tag is managed by the server 50 and transmitted to the lift gate 3A. The server 50 manages the ticket number and the device ID 41 of the attachment device 10 with the ticket number and the device ID 41 related to each other.

The sensor controlling section 33 controls the sensor section 12 to acquire the sensor information. Specifically, the sensor controlling section 33 supplies the sensor section 12 with electric power to activate the sensor section 12, sets sampling time, acquires the sensor information, and stores the acquired sensor information in the memory section 40. The sampling time is produced on the basis of an oscillating clock produced by a real-time clock (not shown). The sensor controlling section 33 acquires data on the time, position, moving speed, and moving direction from the positioning sensor 13 in the sensor section 12 and data on the time, inclination, and travel from the acceleration sensor 15 in the sensor section 12 and chronologically memorizes the information as sensor information data 43 in the memory section 40.

The communication processing section 35 controls the communication section 21 to cause it to transmit the sensor information. In detail, the communication processing section establishes communication with the server 50 via the communication section 21 and the communication antenna 5, reads the sensor information data 43 memorized in the memory section 40, and transmits the sensor information data 43 along with the device ID 41 to the server 50. To achieve a speed close to a real-time speed, the communication processing section 35 may keep establishing communication with the server 50 and transmit the sensor information acquired from the sensor controlling section 33 to the server 50 concurrently with the acquisition.

Further, the communication processing section 35 accepts a reception interrupt process from the communication section 21 and activates the notification information processing section 37.

The notification information processing section 37, when there is information of which the player should be notified, identifies and outputs information of which the notification section 16 needs to be notified. Specifically, when the server 50 specifies a plurality of device IDs or a single device ID as a target of notification and the notification information processing section 37 receives an interrupt signal representing, for example, "going-off-course information," the notification information processing section 37 of an attachment device 10 outputs a notification signal representing warning to the notification section 16 in a case where the received notification target device IDs contain the device ID 41 of the attachment device 10. For example, as the interrupt signal, a signal based on the UDP (user datagram protocol), which is the transport layer of IP, is broadcast from the server 50. The UDP, which is a protocol having a speed close to a real-time speed, is used because urgent broadcast is required. The distributed signal contains a command code representing the going-off-course information and information on the notification target device ID of the attachment device 10 attached to a player who is the target of notification of the going-off-course information.

The notification information processing section 37 of an attachment device 10, when it receives the command code and the information on the notification target device IDs and determines that the notification target device IDs contain the device ID 41 of the attachment device 10, transmits a notification signal, such as a continuous blink output signal that causes the LED 18 to continuously blink or a buzzer sound continuous output signal that causes the busses 19 to continuously output sound, to the notification section 16. The player, when notified of the notification signal, can grasp that the player will be in danger of some kind. Further, in a case where a notification pattern of the notification signal and the content of the notification are related to each other, the player who is notified of the notification signal can determine that the notification signal represents the "going-off-course information" or is another danger signal. For example, the notification pattern is configured as follows: the state in which the LED 18 continuously emits yellow light represents "You have possibly gone out of the course (by a distance of about 1 m);" the state in which the LED 18 emits yellow light but blinks represents. "You have gone out of the course (by a distance of at least 2 m);" and the state in which the LED 18 continuously emits red light represents "Highly urgent warning due, for example, to an avalanche or a tornado."

The memory section 40 is formed of a ROM, a flash ROM, a RAM, an FeRAM (registered trademark) (ferroelectric RAM), or any other memory device and memorizes a variety of programs (not shown) including a control program for achieving the functional sections of the control section 30, data, and other pieces of information. The memory section 40 further has a work area that temporarily memorizes data being processed, variables, flag values, processed results, and other factors in a variety of processes. The memory section 40 further stores the device ID 41 and the sensor information data 43 described above and other pieces of information.

Server

The server 50 includes the communication section 51, an operation section 53, a display section 55, a processing section 60, and a memory section 80.

The communication section 51 is a communication adaptor that performs communication with the attachment device 10 and communication with the lift gates 3. The communication section 51 transmits and receives a wireless signal to and from the attachment device 10 via the communication antenna 5 so that communication with the attachment device 10 using a common communication protocol is performed for a variety of data. The communication section 51 is wired or wirelessly connected to the lift gates 3 and transmits and receives a ticket number a result of the gate operation or whether or not the gate was opened, the time when the ticket number was examined, and other pieces of auxiliary information to and from the lift gates 3.

In a case where the display apparatus 7 have a data communication function, the communication section 51 establishes communication with the display apparatus 7 and transmits screen information and other pieces of information by using a common communication protocol.

The operation section 53 is an input device, such as a keyboard and a mouse. The operation section 53 may instead be a touch panel that covers the display surface of the display section 55. The operation section 53 outputs an inputted operation signal to the processing section 60.

The display section 55 is formed of a liquid crystal panel as a preferable example. The display section 55 can display all display screens generated under the control of the processing section 60. The display section 55 corresponds to a display apparatus that can be viewed in a network environment and the notification section set forth in the appended claims.

Processing Section

The processing section 60 is a CPU and controls the sections that form the server 50, such as the communication section 51, the operation section 53, the display section 55, and the memory section 80.

The processing section 60 executes a program 99 memorized in the memory section 80 to achieve the registration section 61, an acquisition section 63, a learning section 66, a generation section 70, and a display processing section 79, each of which is a functional section. The functional sections described above are presented only by way of example and all the functional sections are not necessarily provided as essential components. Further, another functional section in addition thereto may be added as an essential component.

Registration Section/Processing Section

The registration section 61 registers an attachment device 10 lent when a lift ticket is purchased in the server 50. In detail, the registration section 61 issues a ticket number when a player purchases a lift ticket. The ticket number is an identification number assigned for each attachment device 10, and the device ID similarly assigned to each attachment device 10 (device ID 41 stored in memory section 40) may also serve as the ticket number. In the following description, it is assumed that the device ID contains the ticket number. That is, it is assumed that a lift ticket has been purchased as long as a device ID is given.

The registration section 61 numbers a device ID and registers the device ID in a device ID list 83 in a device management DB 82. The device ID list 83 stores device IDs and information on the lift ticket related to each of the device IDs. The registration section 61 controls the communication section 51 to cause it to transmit the device IDs and information associated therewith to the lift gates 3. The associated information is, for example, the expiration time of a lift ticket (until 12:00 in the case of a half-day ticket). As described above, at the timing when the registration section 61 registers a device ID, the device ID has already stored as the device ID 41 by the ticket processing section 31 of the attachment device 10.

Acquisition Section/Processing Section

The acquisition section 63 acquires the sensor information from the attachment devices 10. In detail, the acquisition section 63 controls the communication section 51 to cause it to receive the sensor information from the attachment devices 10 via the communication antenna 5. The acquisition section 63 sorts the received pieces of sensor information on a device ID basis and stores the pieces of sensor information in a device information table 84 in the device management DE 82. The pieces of sensor information are chronologically stored in sensor information data 85 in the device information table 84. As described above, each of the pieces of sensor information contains the time, position, moving speed, moving direction, inclination, travel, and other data.

Further, the acquisition section 63 extracts data on a trajectory (chronologically stored positions) on a device ID basis and invokes the function of the learning section 66 to acquire course trajectories, course widths, and divided areas corresponding to the trajectory data. The acquired information on the course trajectories, the course widths, and the divided areas is stored in course information 87 in the device information table 84. The acquisition section 63 corresponds to the acquisition section set forth in the appended claims, and the sensor section 12 and the sensor control section 33, which are provided in the attachment device 10 and acquire the sensor information can also be considered as the acquisition section.

Overview of Learning Section/Processing Section

The learning section 66 receives, as input information, the trajectories along which players have practiced sliding actions (sensor information from attachment devices 10) and determines and outputs the course trajectories and the course widths, which determine the shapes of sliding action courses, and the divided areas. The learning section 66 further has the function of analyzing a large number of player sliding action situations stored in the device management DB 82, correcting the course trajectories, the course widths, and the divided area when they should be corrected, and outputting the corrected result. The learning section 66 carries out a course initial setting process in order to collect information on the initial state of each course. In the course initial setting process, a player who works for the skiing ground practices a sliding action multiple times with the attachment device 10 attached to the player while checking the condition and other factors of the skiing ground. The initial state of the course trajectories, the course widths, and the divided area on the skiing ground is thus acquired.

Each of the course trajectories is a trajectory representing a course where a person is allowed to practice a sliding action and which includes the courses C1, C2, and C3 described above. These courses have been derived by learning section 66 on the basis of sliding action trajectories along which the player had actually practiced sliding actions. Each of the course to corresponds to the trajectories along which players practice actions set forth in the appended claims.

Each of the course widths represents the width of a sliding action practicable region along a course trajectory. The width of the sliding action practicable area is calculated on the basis of trajectories of sliding actions practiced by a plurality of players on the same course. Each of the course widths corresponds to the width of the area where players are allowed to practice actions set forth in the appended claims.

Each of the divided areas is a sliding action practicable region fragmented on the basis of a branch point on a sliding action course, the degree of easiness of the course, or any other characteristic of the course. In the following description, it is assumed that the entire area is divided into divided areas, an area A1, an area A2, an area A3, an area A4, and area A5, and an area A6. Each of the divided areas A1 to A6 corresponds to the area set forth in the appended claims.

The learning section 66 includes a course trajectory learning section 67, a divided area learning section 68, and a course width learning section 69 and determines the course trajectories, the course widths, and the divided areas described above. Information on the determined course trajectories, the course widths, and the divided areas is stored as course information data 90 in the memory section 80. The learning section 66 will be described later in detail with reference to FIG. 8.

Generation Section/Processing Section

Figure 5:
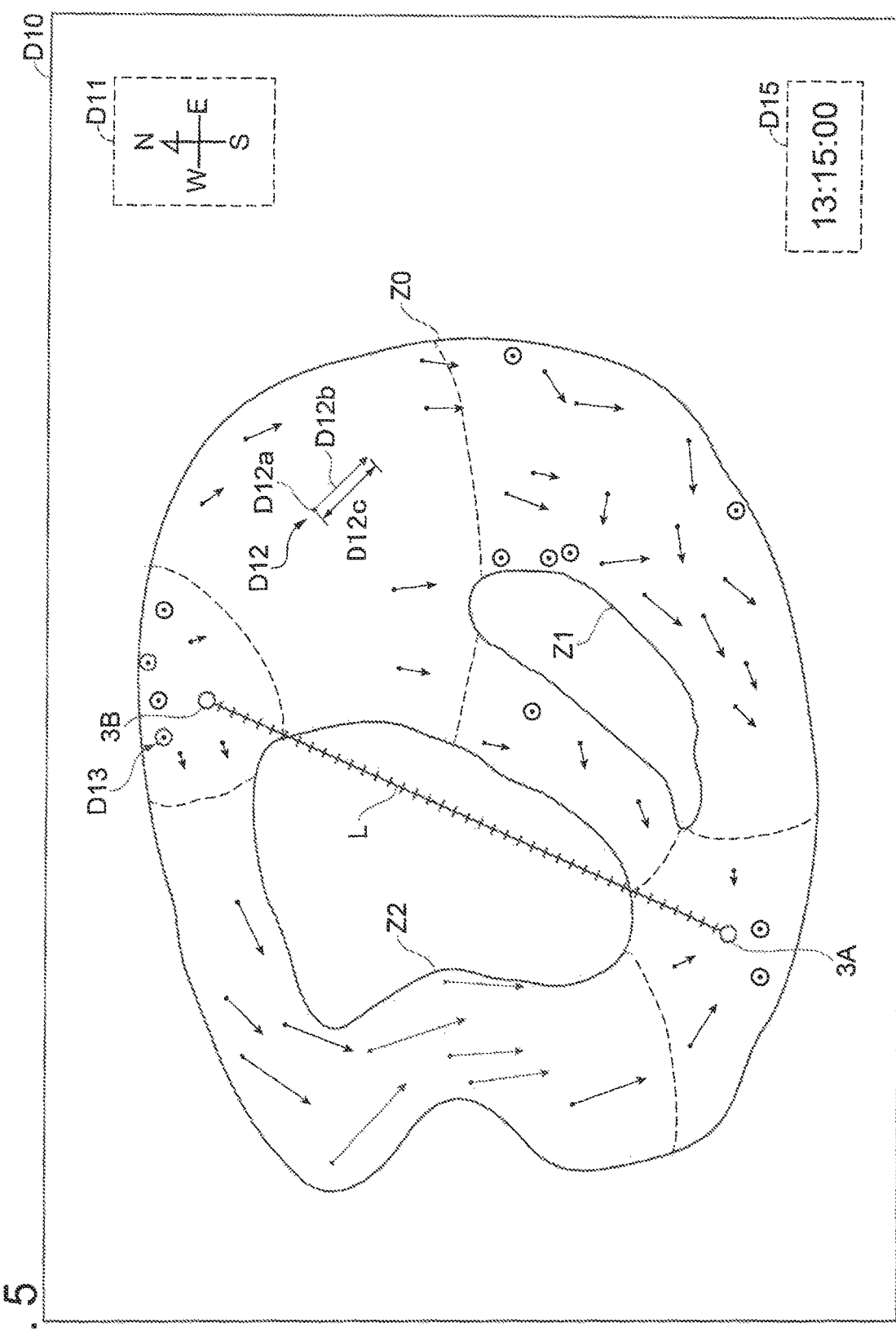
FIG. 5 shows an example of an analysis map screen.
Figure 6:
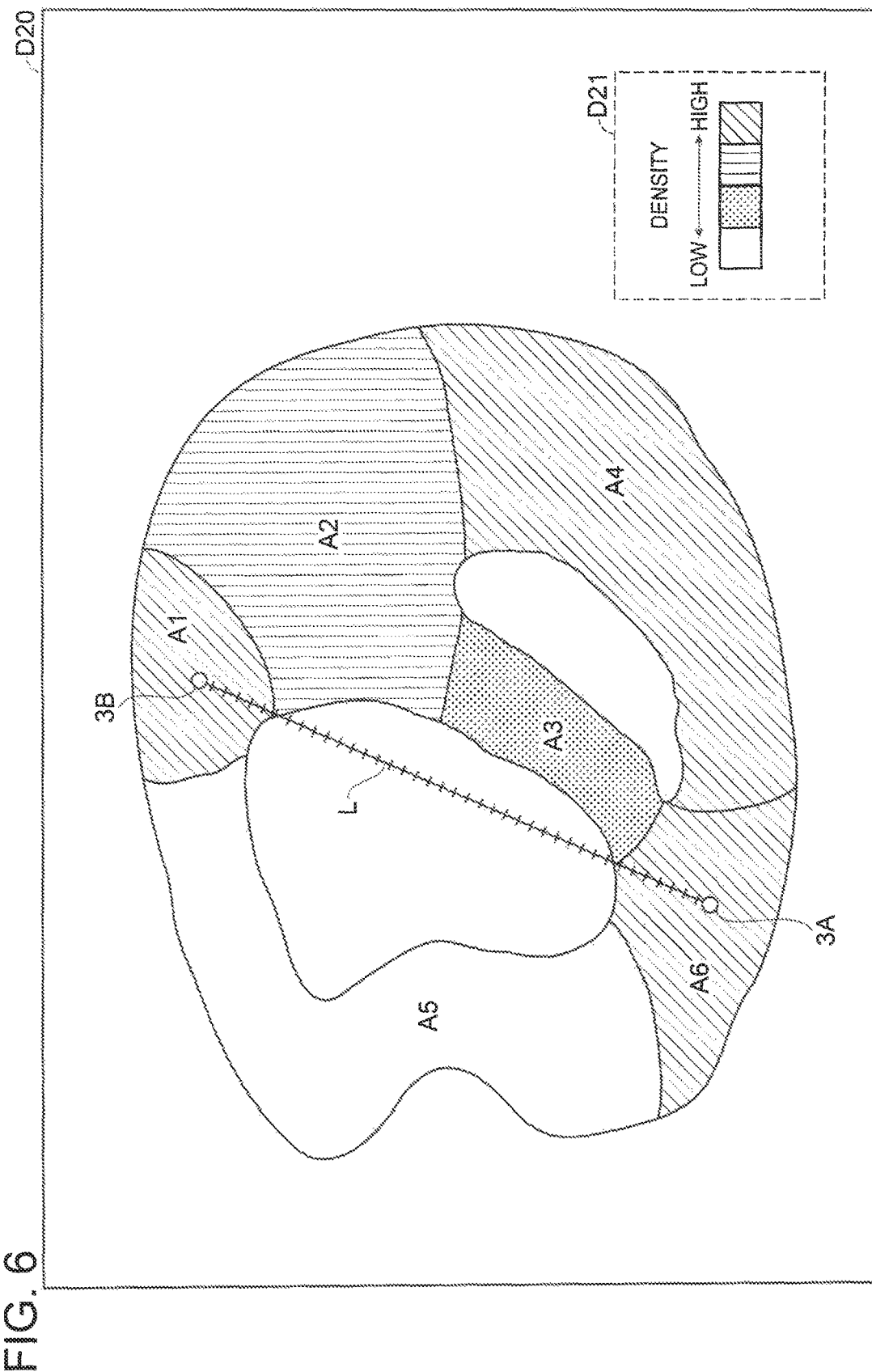
FIG. 6 shows an example of a density map screen.
Figure 7:
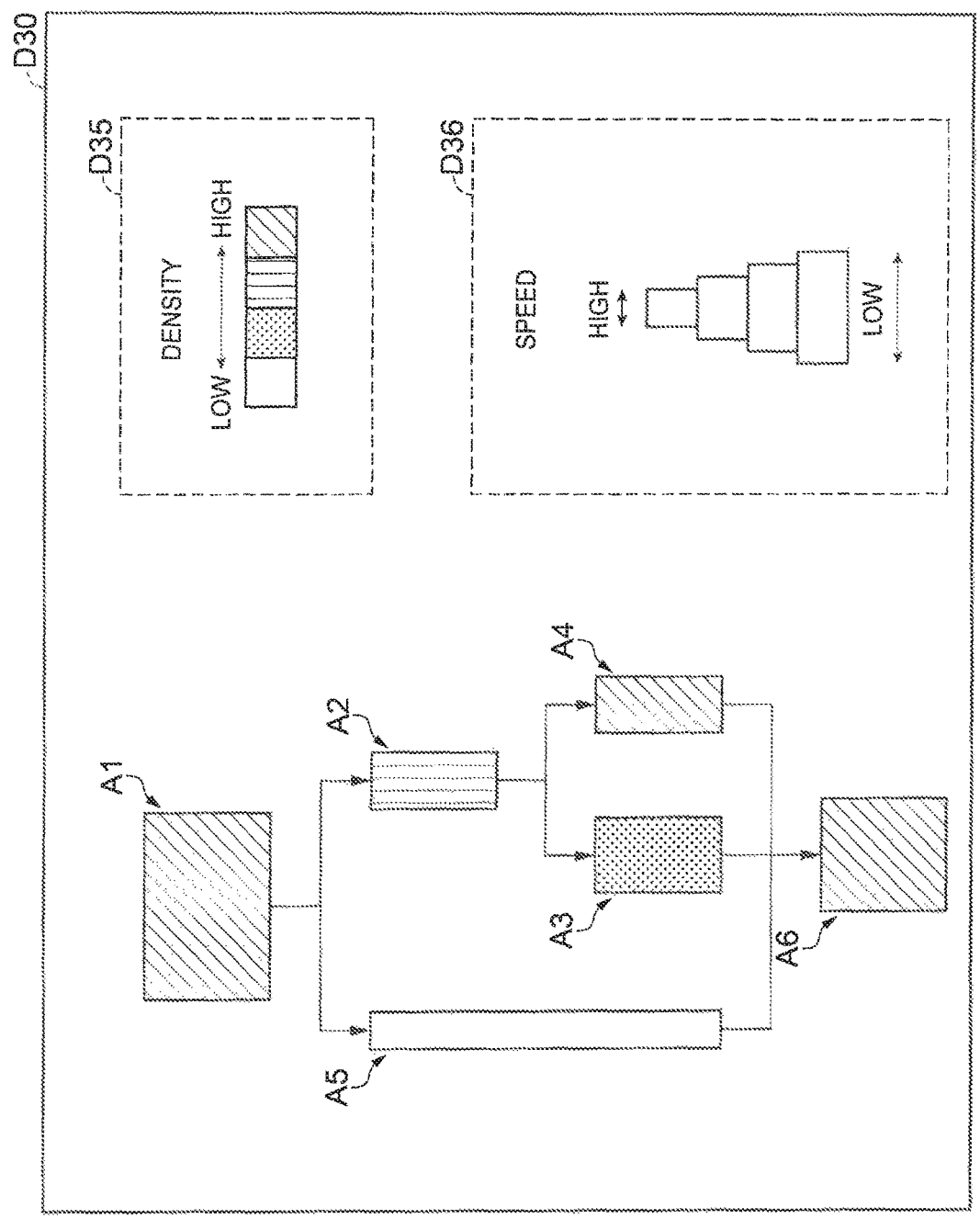
FIG. 7 shows an example of an analysis graph screen.

The generation section 70 will be described with reference to FIGS. 5 to 7. FIG. 5 shows an example of the analysis map screen. FIG. 6 shows an example of the density map screen. FIG. 7 shows an example of the analysis graph screen.

The generation section 70 generates information representing the smoothness of players' movement and generates display screens that visually convey the information. The display screens are specifically formed of the analysis map screen (screen D10 in FIG. 5), the density map screen (screen D20 in FIG. 6), and the analysis graph screen (screen D30 in FIG. 7). The analysis map screen, the density map screen, and the analysis graph screen and information for generating the display screens correspond to the area situation information set forth in the appended claims. The generation section 70 further senses an attachment device 10 (player) that goes out of the course width along a course trajectory and generates going-off-course information of which the player is notified.

The generation section 70 includes an analysis map generation section 71, a density map generation section 73, an analysis graph generation section 75, and a going-off-course information generation section 77.

The analysis map generation section 71 generates the analysis map screen (screen D10), which is one of the display screens. The screen D10 is a screen in which the positions of players or the density of the players and the moving speeds thereof are displayed on a map of the region Z0. In the screen D10, the regions Z0, Z1, and Z2, the lift L, the lift gate 3A, and the lift gate 35 shown in FIG. 1 are displayed on the map In the region Z0, a black dot with an arrow and a symbol formed of a black dot surrounded by a circle are displayed at a plurality of locations. One black dot corresponds to one player. Each black dot surrounded by a circle (mark D13) represents the state in which a stationary player is present in the position. Each black dot with an arrow (mark D12) represents the state in which the player is moving. The position of a black dot displayed on the map represents the player's position, and the state of the distribution of the black dots on the map represents the density of the players.

In an upper right portion of the display screen are displayed cardinal points D11, which represent the orientation on the map including the area Z0, and in a lower right portion of the display screen is displayed time D15, which is updated time information "13:15:00."

The mark D12 will be described. The mark D12 is formed of a black dot D12$a$ and an arrow D12$b$. The arrow D12$b$ represents southeast orientation with reference to the cardinal points D11 on the screen. A line segment D12$c$ represents the length of the arrow D12$b$ and in turn represents the player's moving speed. The greater the length of the line segment D12$c$, the higher the moving speed, whereas the smaller the length, the lower the moving speed.

The analysis map generation section 71 selects all attachment devices 10 in the device management DB 82 whenever a fixed period (one second, for example) elapses and reads the latest sensor information data 85 associated with the attachment devices 10. The analysis map generation section 71 generates figures having the shapes shown by the marks D12 and D13 on the basis of the positions, the moving speeds, and the moving directions contained in the sensor information and places the figures on the screen D10. The analysis map generation section 71 further displays the read time as the time D15.

The density map generation section 73 generates the density map screen (screen D20), which is one of the display screens. The screen D20 is a screen in which the density of players is displayed on the map on a region basis in each of the regions A1 to A6. On the screen D20 are displayed the regions Z0, Z1, and Z2, the lift L, the lift gate 3A, and the lift gate 3B shown in FIG. 5. The region Z0 is partitioned into the regions A1 to A6, and the regions are filled with different patterns. The patterns are explained in an explanation field D21. In the explanation field D21, the population density (hereinafter referred to as density)) of the players is expressed by four patterns. Each of the regions A1, A4, and A6 is displayed by using a highest density pattern, the region 2 is displayed by using a second highest density pattern, the region A3 is displayed by using a third highest density pattern, and the region A5 is displayed by using a lowest density pattern. The patterns may be replaced with or may be combined with different colors assigned to the different densities.

The density map generation section 73 divides the number of players present in each of the divided areas by the surface area of the divided area to calculate the density. The number of players can be determined on a divided area basis by referring to the device ID list 83 in the device management DE 82 and the course information 87 in the device information table 84. The surface area of a divided area has been calculated by the learning section 66 The density map generation section 73 selects the pattern according to the calculated density and places the pattern on the screen D20.

The analysis graph generation section 75 generates the analysis graph screen (screen D30), which is one of the display screens. The screen D30 is a display screen formed of graphs diagrammatically showing the density and the moving speeds of the players on a divided area basis. The analysis graph screen visually and intuitively conveys the density and the moving speeds (speed), which represent smoothness of the players' movement and easiness of the divided area, and other pieces of information to the players.

On the screen D30 are displayed rectangles representing the regions A1 to A6, which are so displayed that the region A1 branches into the region A5 and the region A2, the region A2 branches into the region A3 and the region A4, and the region A5, the region A3, and the region A4 merge into the region A6. Each of the regions is filled with one of the patterns shown in an explanation field D35. The patterns are the same as those shown on the screen D20. The width of the rectangle representing each of the regions represents a speed. The speed is the average of the moving speeds of the players who practice sliding actions in the region. As shown in an explanation field D36, the narrower the width of the rectangle, the higher the speed, whereas the wider the width of the rectangle, the lower the speed.

The analysis graph generation section 75 averages the moving speeds of a plurality of players present in each of the divided areas to calculate the speed. A player s moving speed is read from the sensor information data 85 in the device information table 84 in the device management DB 82. Since the density map generation section 73 acquires device IDs present in each of the divided areas, the analysis graph generation section 75 sums the latest moving speeds related to the device IDs and divides the sum by the number of device IDs to calculate the average.

The analysis graph generation section 75 uses the pattern corresponding to the density of each of the divided areas calculated by the density map generation section 73 and the average of the moving speeds to generate a rectangle on a divided area basis and places the rectangle on the screen D30.

As described above, the generation section 70 generates the screens D10, D20, and D30 and places the screens on the screen D1. Simultaneously displaying the screens D10, D20, and D30 allows the players to visually grasp a sliding action practicable course on the skiing ground and the degree of congestion and smoothness of the players' movement in each of the divided regions.

The generation section 70 further includes the going-off-course information generation section 77. The going-off-course information generation section 77 generates going-off-course information when a player moves out of a sliding action practicable region. A region outside a sliding action practicable region is a region which is located within the region A0, which is the entire site of the skiing ground, and where a player is not allowed to practice a sliding action. The region outside the sliding action practicable region (sliding action impracticable region) in the descriptive diagram of FIG. 1 formed, for example, of a region that is located within the region A0 but outside the region Z0 and regions within the region Z1 or Z2. The going-off-course information generation section 77, when it detects that the position of an attachment device 10 is located in any of the sliding action impracticable regions, generates the going-off-course information of which the player is notified and controls the communication section 51 to cause it to transmit the going-off-course information to the attachment device 10.

The attachment device 10 having received the going-off-course information processes the going-off-course information in the notification information processing section 37, and the notification section 16 notifies the player of the going-off-coarse information. The content of the going-off-course information generated by the notification information processing section 37 is, for example, "You have possibly gone out of the course (by a distance of about 1 m)" or "You have gone out of the course (by a distance of at least 2 m)" as described above. The going-off-course information generation section 77 can derive the contents of the going-off-course information also by using the position and the moving speed of the attachment device 10.

The notification information processing section 37 further generates a danger signal, such as "Highly urgent warning due, for example, to an avalanche or a tornado." When the going-off-course information generation section 77 receives such information on danger from the operation section 53 or an external system (information from Meteorological Agency or any other authority), the going-off-course information generation section 77 transmits information corresponding to the danger signal to all attachment devices 10 (device IDs).

The sliding action practicable regions in the region A0 have been learned and corrected as required by the learning section 66. The sliding action impracticable regions therefore change. In this case, for example, the going-off-course information is transmitted to a player (attachment device 10) who enters a sliding action impracticable region for the first time, but the sliding action impracticable region is thereafter learned as a sliding action practicable region in some cases when the region is determined to be safe afterward.

Display Processing Section/Processing Section

The display processing section 79, which is a functional section that controls a display destination, switches the display destination from one to another and outputs the display screens generated by the generation section 70 to the selected display destination. Specifically, the display processing section 79 selects any of the display apparatus 7A and 7B of the display apparatus 7, the display section 55, and the communication section 51, converts the display screen display format into a format suitable for the selected display destination, and outputs the display screens. The display screens to be outputted are the screens generated by the generation section 70. The display processing section 79 may reconstruct each of the screens generated by the generation section 70, for example, in an HTML format, which allows the screen to be displayed as a Web page. In this case, an external display apparatus or information apparatus equipped with a web browser or any other application program may acquire a webpage formed by the display processing section 79. The webpage may be acquired at an arbitrary point of time or whenever a fixed period elapses. The display processing section 79 corresponds to the function of part of the notification section set forth in the appended claims.

Memory Section

The memory section 80 is formed of a ROM (read only memory), a flash ROM, a RAM (random access memory), or any other memory device and memorizes a variety of programs for achieving the functional sections of the processing section 60, data, and other pieces of information. The memory section 80 further has a work area that temporarily memorizes data being processed, variable values, processed results, and other factors in a variety of processes. The memory section 80 is equipped with a database engine such as a relational database, and the database engine carries out a variety of processes, such as registration, update, deletion, and search of data managed by the device management DB 82, and a transaction process.

The memory section 80 stores (memorizes) the device management DB 82, the course information data 90, analysis map screen data 91, density map screen data 93, and analysis graph screen data 95 stored by the generation section 70, and the program 99.

The device management DB 82 manages the device ID list 83 and the device information table 84. The device information table 84 stores the sensor information data 85 and the course information 87.

The device ID list 83 stores the device IDs of all attachment devices 10 used on the skiing ground. The device information table 84 stores the sensor information data 85 and the course information. 87 on a device ID basis. The sensor information data 85 stores pieces of the sensor information in a chronological manner, and the course information data 90 stores the course trajectories, the course widths, and the divided areas corresponding to the pieces of the sensor information.

The analysis map screen data 91 is a display screen generation work area used by the analysis map generation section 71.

The density map screen data 93 is a display screen generation work area used by the density map generation section 73.

The analysis graph screen data 95 is a display screen generation work area used by the analysis graph generation section 75.

The program 99, when it is read and executed by the processing section 60, achieves the functions of the functional sections of the learning section 66, the generation section 70, and other sections contained in the processing section 60. The processes described above will be described later with reference to a flowchart. The program 99 corresponds to the program set forth in the appended claims.

Learning Section

The learning section 66 will be described in detail with reference to FIG. 8.

Figure 8:
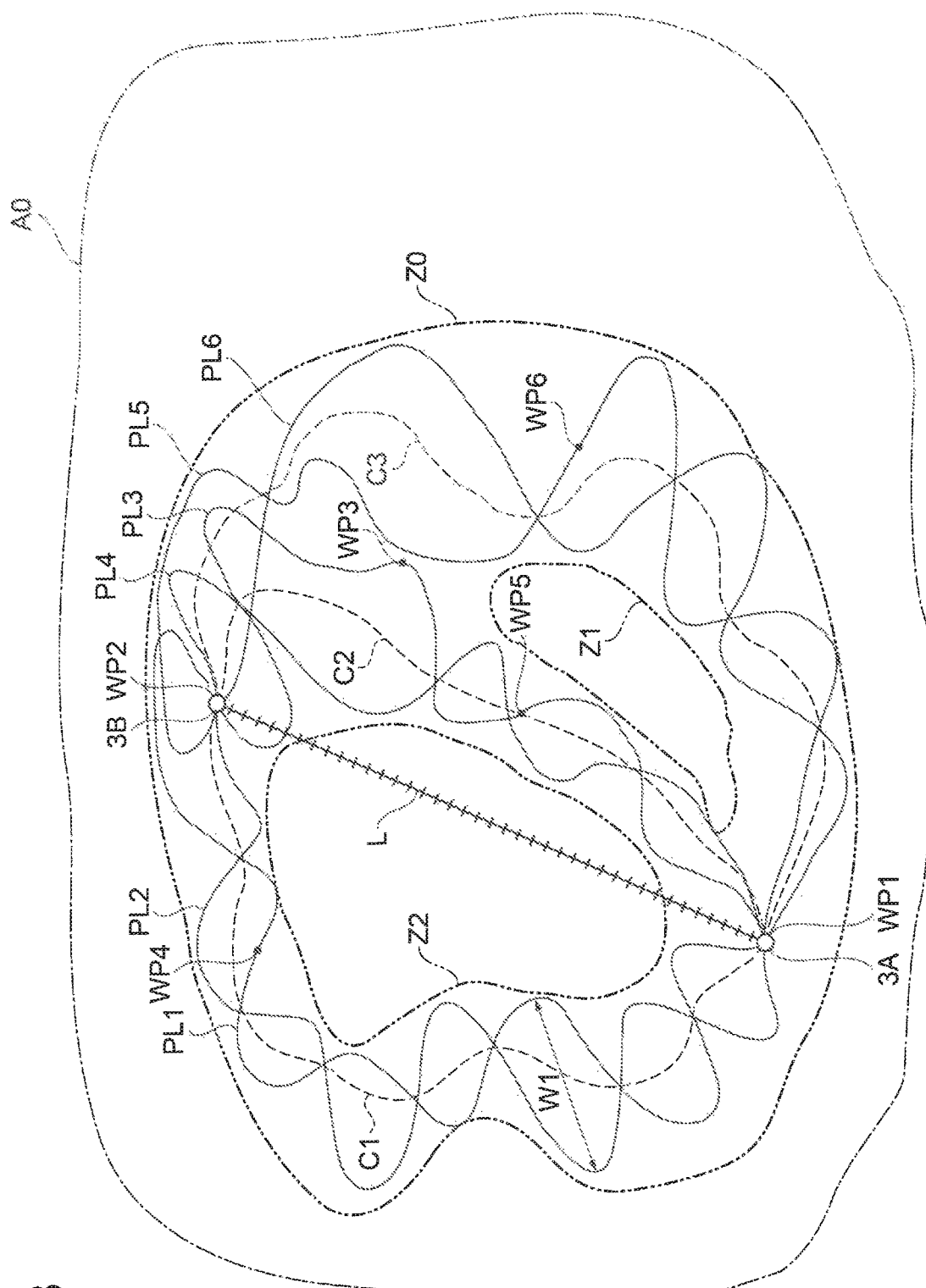
FIG. 8 describes course learning.

FIG. 8 describes course learning. The descriptive diagram shown in FIG. 8 shows the region A0, the lift L, the lift gate 3A, and the lift gate 3B shown in FIG. 1.

The learning section 66 uses players' sliding action trajectories as input information to determine and output the course trajectories and the course widths, which determine the shapes of sliding action courses, and the divided regions. A trajectory PL1, a trajectory PL2, a trajectory PL3, a trajectory PL4, a trajectory PL5, and a trajectory PL6 shown in FIG. 8 are each a player's sliding action trajectory and input information. The trajectories may be trajectories of sliding actions practiced by the same player or trajectories of sliding actions practiced by a plurality of player. The course C1, the course C2, and the course C3 shown in FIG. 8 are course trajectories to be outputted, and a course width W1 is an example of the course width of the course C1. How to determine divided regions to be outputted will be described later.

The present description will be first made of the course initial setting process carried out by the learning section 66 by way of example. That is, before a player practices a sliding action, only the region A0, which is the entire site of the skiing ground, the lift L, the lift gates 3A and 3E have been determined, and the other regions Z0, Z1, and Z2, which represent sliding action practicable regions, and the sliding action courses C1, C2, and C3 are undetermined. After the initial setting process is carried out, the regions Z0, Z1, and Z2 and the sliding action courses C1, C2, and C3 are determined. After the sliding practicable regions and the sliding courses are determined, a plurality of players practice sliding actions along any of the sliding action courses. The sliding action courses and the sliding action practicable regions are corrected also by the sliding action trajectories of the plurality of subsequent players.

The procedures of the initial setting process are listed below.

Procedure 1: Set passage points (waypoints)
Procedure 2: Extract trajectories that do not pass through the waypoints
Procedure 3: Repeat the procedures 1 and 2 for different trajectories and waypoints The procedures 1 to 3 described above are repeated. A specific example will be shown below.

Procedure 1

Three waypoints are set as follows: The lift gate 3A is set as a point WP1; the lift gate 33 is set as a point WP2; and an arbitrary passage point on the trajectory PL3 is set as a point WP3. Each of the waypoints contains information on the latitude, longitude, and altitude.

Procedure 2

The distance from the point WP3 to each of the trajectories PL1 to PL6 (excluding PL3) is calculated. A trajectory for which the calculated distance is greater than or equal to a predetermined distance (about 20 m, for example) is extracted. In this case, the distances to the trajectories PL1 and PL2 were greater than or equal to the predetermined distance, and the distances to the trajectories PL4 to PL6 were smaller than the predetermined distance.

Procedure 3/Determination of Course C1

A point WP4 is set at an arbitrary passage point on the trajectory PL1. The distance between the point WP4 and the trajectory PL2 is calculated. The distance between the point WP4 and the trajectory PL2 is smaller than the predetermined distance, and the trajectories PL1 and PL2 are therefore classified into the same trajectory group and determined to be the course C1. In this case, the same process may be repeated for other waypoints on the trajectory PL1 to check if the calculated distances between the trajectory PL2 and the other waypoints are all smaller than the predetermined distance.

Procedure 3/Determination of Course C2

A point WP5, which is a waypoint different from the point WP3, is set on the trajectory PL3. The distances between the point WP5 and the trajectories PL4 to PL6 are calculated. The trajectory PL4 was a trajectory for which the calculated distance is smaller than the predetermined distance, and the trajectories PL5 and PL6 are trajectories for which the calculated distances are greater than or equal to the predetermined distance. The trajectories PL3 and PL4 are therefore classified into the same trajectory group and determined to be the course C2.

Procedure 3/Determination of Course C3

A point WP6 on the trajectory PL5 is set as a waypoint The distance between the point WP6 and the trajectory PL6 is calculated. The distance between the point WP6 and the trajectory PL6 is smaller than the predetermined distance, the trajectories PL5 and PL6 are therefore classified into the same trajectory group and determined the course C3.

In the initial setting process formed of the procedures described above and carried out by the learning section 66, the sliding action courses C1, C2, and C3 are determined. In the above description, the distances between trajectories and a waypoint are compared with a predetermined distance, and whether or not the trajectories are classified into the same trajectory group is evaluated. Instead of comparison with the predetermined distance, the evaluation may be performed by comparing the calculated distances between the trajectories and the waypoint with one another. For example, to determine the course C2, distances between the point WP5 and the trajectories PL4 to PL6 are calculated. The distance between the point WP5 and the trajectory PL5 and the distance between the point WP5 and the trajectory PL6 are greater than the distance between the point WP5 and the trajectory PL4. Further, the difference between the distance between the point WP5 and the trajectory PL5 and the distance between the point WP5 and the trajectory PL6 is small, and the trajectories PL5 and PL6 are therefore estimated to be close to each other. As a result, the trajectories can be classified into a course determined by the trajectories PL3 and PL4 and a course determined by the trajectories PL5 and PL6.

Determination of Course Width

The course width of a sliding action course is calculated by using a plurality of sliding action trajectories determined to relate to the same course. The course width W1 shown in FIG. 8 is calculated by using the trajectories PL1 and PL2, which relate to the course C1. The course width calculation method will be described with reference to the course width W1. Information on a trajectory is formed of a group of pieces of information on chronologically measured points. Let PL1(i) (i=1 to n) represent the trajectory PL1. Distances D(i) (i=1 to n) between PL1(i) and the trajectory PL2 are calculated. The distances between PT1(i)and all points on the trajectory PL2 are calculated, and the minimum of the calculated distances is substituted into the distance D(i). The distance D(i) is the distance between each point on the trajectory PL1 and the trajectory PL2, and the maximum of the distances D(i) is determined to be the course width W1 (course width).

The course width W1 may instead be calculated by using the altitude contained in each trajectory. For example, the distance between the positions located on the trajectories PL1 and PL2 and containing altitudes closest to each other may be calculated for each altitude, and the maximum of the group of the calculated distances may be set to be the course width W1.

Determination of Divided Areas

A method for determining a divided area that reflects the characteristics of a branch point on a sliding action course will be described. At the waypoints described above, consider overlap of sliding action courses with each other. Reference character "&" means the overlap.

At the point WP2, the course C1 & the course C2 & the course C3 is satisfied.

At the point WP3, the course C2 & the course C3 is satisfied.

At the point WP4, only the course C1 can be chosen.

At the point WP5, only the course C2 can be chosen.

At the point WP6, only the course C3 can be chosen.

At the point WP1, the course C1 & the course C2 & the course C3 is satisfied.

The description will be made of a case where the region A1, which is a divided area, is determined. The region A1 is a region where a sliding action course can be selected from a plurality of courses. Specifically, it is obvious that the point WP2 is a branch point leading to the course C2 & the course C3, which lead to the point WP3 following the point and the course C1, which leads to the point WP4 following the point WP2. That is, a player in the vicinity of the point WP2 can select one of the two sliding action courses, the course C2 & the course C3 or the course C1. Sliding trajectories along the trajectories PL1 to PL6 in the vicinity of the point WP2 are next analyzed. For example, the trajectory PL5 starts from the point WP2 and first proceeds toward the course C1 but then moves toward the course C2 & the course C3 and proceeds along the course C3. That is, the trajectory PL5 allows selection of a plurality of courses until a point closest to the course C1 is reached. By analyzing the sliding action trajectories PL1 to PL6 as described above, a region where a course can be selected from a plurality of courses is determined to be a divided area. In this case, a region in the vicinity of the point WP2 can be determined to be the region A1 (see FIG.6). The regions A2 to A6 shown in FIG. 6 are similarly determined to be divided areas.

A method for determining a divided area that reflects the easiness of a sliding action course or any other characteristic will be described. The method uses the moving speeds contained in the sensor information associated with the trajectories PL1 to PL6. For example, in the method, the tendency of the moving speeds is analyzed in the chronological order, and a region where a slow movement tendency is detected, a region where a fast movement tendency is detected, a region between the fast movement tendency region and the slow movement tendency region, or any other region is determined to be a divided area. For example, in the vicinity of the lift gate 3B, the moving speed tends to be low because players wonder, for example, about sliding action course selection in many cases. A region showing a low moving speed tendency is determined to be one of the divided areas. For example, the region A1 corresponds to a region showing a low moving speed tendency.

The learning section 66 thus carries out the course initial setting process to determine the course trajectories, the course widths, and the divided areas. On a skiing ground, since the conditions thereof change day after day due to natural phenomena, such as changes in the temperature, humidity, and weather, and the course trajectories, the course widths, and the divided areas change accordingly, the initial setting process is preferably carried out on a daily basis during the business period of the skiing ground. In a case where there is night skiing operation, carrying out the initial setting process before the night skiing operation starts allows correct setting of course trajectories, course widths, and divided areas only for the night period.

Even after the course initial setting process is carried out, the learning section 66 uses sliding action trajectories collected from a plurality of players who are customers of the skiing ground to correct the course trajectories, the course widths, the divided areas, and other factors by using the same method used in the initial setting process. The course trajectories, the course widths, and the divided areas are corrected in accordance with the sliding action skills and eliding action methods of players on the skiing ground (such as powerful sliding action, sliding action practiced as training, and low-speed sliding action). The correction process carried out by the learning section 66 is preferably carried out after the information on the course trajectories, the course widths, and the divided areas in a previous timeframe is canceled (deleted, for example). Carrying out the correction process in addition to the initial setting process allows exact correction of the sliding action practicable course trajectories, course widths, and divided areas that vary depending on a timeframe, for example, even in a case where sliding actions can be practiced in the morning over a wide range on the skiing ground but the sliding action practicable range narrows in the afternoon.

The learning section 66 has, in preparation for a request from another functional section (acquisition section 63, for example), the function of accepting data on an arbitrary player's trajectory, calculating the corresponding course trajectories, course widths, and divided areas, and outputting information on the above factors. A method of the calculation includes comparing the data on the arbitrary trajectory with waypoints (points WP1 to WP6) sliding action courses (trajectories C1 to C3), and divided areas (regions A1 to A6) having been already determined and selecting a waypoint and a sliding action course closest to the data on the arbitrary trajectory and a divided area containing the data on the arbitrary trajectory. The learning section 66 calculates course trajectories, course widths, and, divided areas on the basis of the information on the selected waypoint, sliding action course, and divided area and outputs the calculated result to the requesting functional section.

The learning section 66 has, in preparation for a request from another functional section (density map generation section 73, for example), the function of calculating the surface area of a specified divided area and outputting the calculated area to the requesting functional section. The method of the calculation includes multiplying the length of the course trajectory in the divided area by the course width. Instead, the area may be determined by integration of the distance D(i) along the course trajectory in the divided area.

Information Notification Method

Figure 9:
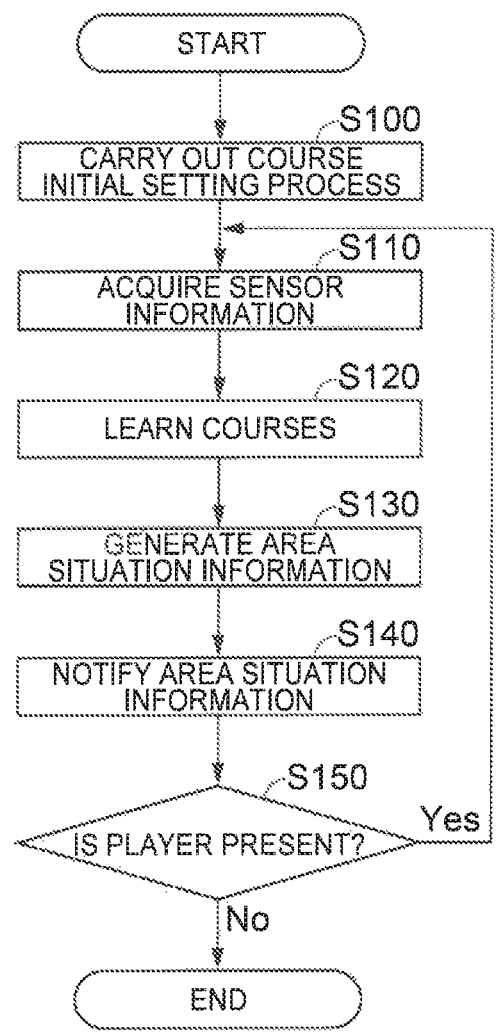
FIG. 9 is a flowchart showing the procedure of an information notification process.

FIG. 9 is a flowchart showing the procedure of an information notification process. The procedure shown in FIG. 9 is carried out by the processing section 60 that controls the communication section 51 and other sections on the basis of the program 99 stored in the memory section 80. The procedure corresponds to the information notification method set forth in the appended claims, and the program 99 corresponds to the program set forth in the appended claims.

In step S100, the course initial setting process is carried out (learning section 66). In detail, the function of the course initial setting process activated, the course trajectories, the course widths, which determine the shapes of sliding action courses, and the divided areas are determined and outputted.

In step S110, the sensor information is acquired (acquisition section 63). In detail, the communication section 51 is so controlled ads to receive pieces of sensor information from attachment devices 10. The received pieces of sensor information are stewed in the device management DB 82 on a device ID basis. The present step corresponds to acquiring information from a sensor attached to each player who is practicing an action in a target area set forth in the appended claims.

In step S120, the courses are learned (learning section 66). In detail, the course trajectories, the course widths, and the divided areas determined in step S100 are corrected as required on the basis of the pieces of sensor information acquired from the plurality of attachment devices 10.

In step S130, the area situation information is generated (generation section 70). In detail, as the area situation information, the analysis map screen, the density map screen, and the analysis graph screen are generated. The steps S10 and S130 correspond to generating area situation information on smoothness of movement of the players in the area on based on the information from the sensors set forth in the appended claims.

In step S140, the area situation information is notified. In detail, the analysis map screen, the density map screen, and the analysis graph screen generated in step S330 are outputted to the display apparatus 7. The present step corresponds to notifying the area situation information set forth in the appended claims.

In step S150, whether or not a player is present is evaluated. In detail, in a case where a player to whom the attachment device 10 is attached is present on the skiing ground (Yes in step S150), the control proceeds to step S110, whereas in a case where no player is present (No in step S150), the entire procedure is terminated.

The process of acquiring the sensor information in step S110 may include the process in which the attachment devices 10 acquire the sensor information (functions of sensor control section 33 and sensor section 12) because the two processes are the same.

As described above, the information notification system 1 according to the present embodiment can provide the following advantageous effects.

The attachment device 10 is attached to each player and detects the sensor information resulting from the player's action. The sensor information contains data on the time, position, moving speed, moving direction, inclination, travel, and other factors of the attachment device 10 detected thereby. The attachment device 10 transmits the sensor information to the server 50. The server 50 (processing section 60) stores the sensor information received from the attachment device 10 in the memory section 80 whenever the server 50 receives the sensor information. The processing section 60 causes the learning section 66 to carry out the course initial setting process to determine the sliding action practicable course trajectories, the course widths, and the divided areas. Further, the processing section 60 uses pieces of sensor information collected from the players to correct the course trajectories, the course widths, and the divided areas whenever the correction is repaired. The generation section 70 of the processing section 60 uses the information on the course trajectories, the course widths, and the divided areas and the pieces of sensor information from the attachment devices 10 to generate the area situation information, such as the analysis map screen (screen D10), the density map screen (screen D20), and the analysis graph screen (screen D30). The screens are display screens that visually convey the players' moving speeds and moving directions, the density and the moving speeds of the players on a divided area basis, and other pieces of information. The display processing section 79 of the processing section 60 outputs the area situation information to the display apparatus 7. The display apparatus 7 are large display apparatus installed in the vicinity of the lift gates 3A and 3B and allow the players to check the players' positions, moving speeds, movement situations, and other pieces of information in each area of skiing ground. The information on the moving speeds and the moving directions (information on smoothness of movement) is information useful for selection of a course suitable for a player's sliding action skill and action sliding method (such as powerful sliding action and slow-sliding action practiced as training).

Further, the information on the smoothness of movement allows a player who visits the skiing ground for the first time or from a remote place so that the player is unfamiliar with the skiing ground to readily locate a coarse that may allow the player to comfortably practice a sliding action. Moreover, the information is also useful for player who practice skiing and a wide variety of other winter sports practiced in a wide variety of playstyles and allows each of the players to select a course where the player can readily move.

Therefore, the information notification system 1, which provides information on smoothness of movement that has not been identified by methods of related art, can assist players who practice skiing and other sports in such a way that the players can practice the sports more comfortably than ever.

Second Embodiment

Figure 10:
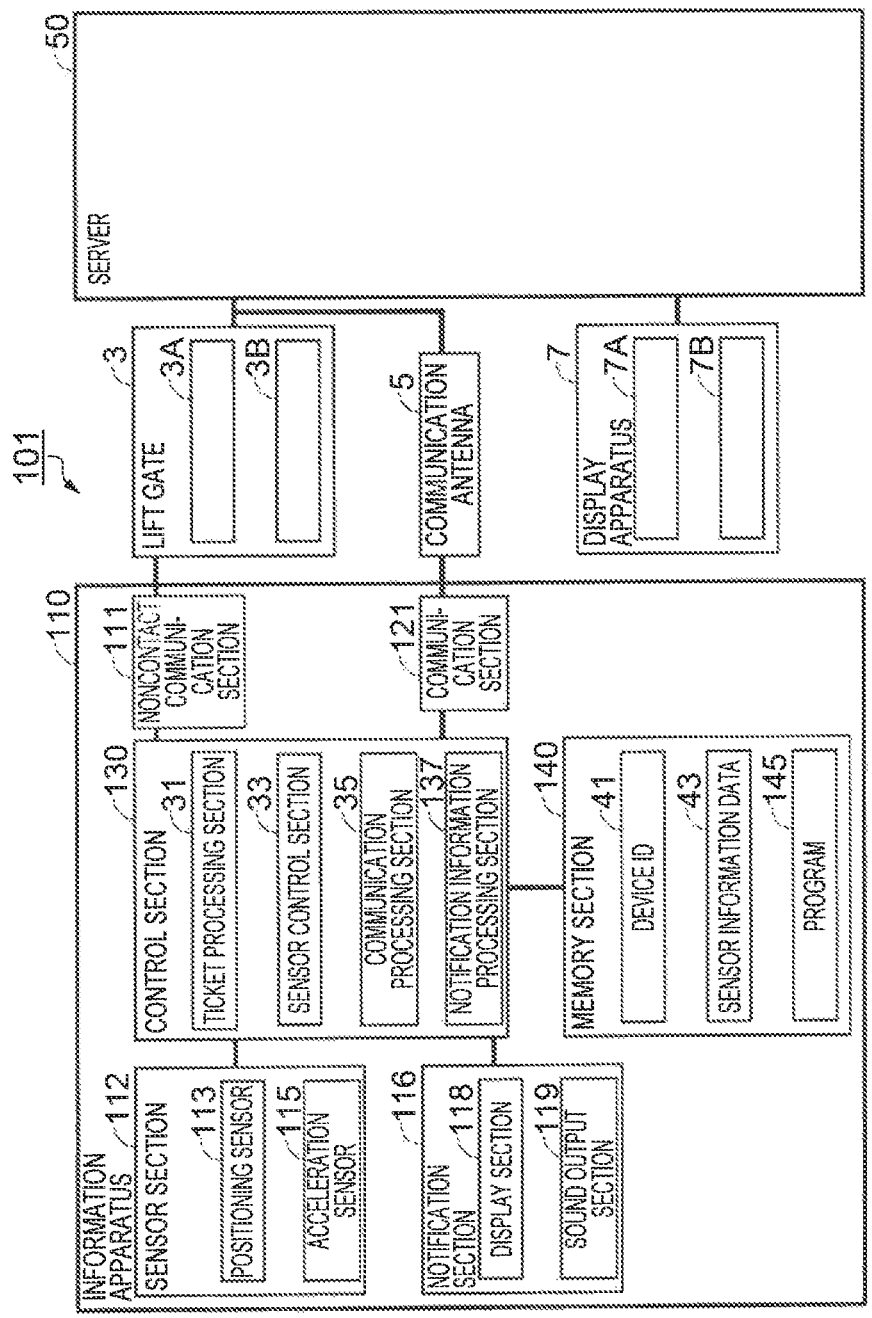
FIG. 10 is a block diagram showing a schematic configuration of an information notification system according to a second embodiment.

FIG. 10 is a block diagram showing a schematic configuration of an information notification system according to a second embodiment. The second embodiment differs from the first embodiment described above, in which the device attached to a player is the attachment device 10 shown in FIG. 2, in that an information apparatus 110 is attached to a player. The server 50, the lift gates 3, the communication antenna 5, and the display apparatus 7 have the same configurations as those in the first embodiment. In the following description, the same configurations as those in the first embodiment have the same reference characters and will not be described in detail. In FIG. 10, the same configurations as those in the first embodiment are partly omitted.

An information notification system 101 is formed of the information apparatus 110, the server 50, the lift gates 3 (3A and 3B), the communication antenna 5, the display apparatus 7 (7A and 7B), and other components.

The information apparatus 110 is a typical smartphone or multifunctional portable terminal and is capable of downloading a program, such as special-purpose software, from an external server or a PC and executing the program. A program 145 stored in a memory section 140 is a program for the information notification system and supplied from a server, such as the server 50, in the information notification system 101. When the program 145 is read and executed by a control section 130, the functions of a ticket processing section 31, a sensor control section 33, a communication processing section 35, a notification information processing section 137, and other functional sections are achieved. These functions are the same functions of the functional sections having the same names in the attachment device 10 (FIG. 4).

The ticket processing section 31 carries out a lift ticket purchase process, the process of memorizing a ticket number in a noncontact communication section 111, and other processes. The player who carries the information apparatus 110 is allowed to pass through the automatic ticket examiner of the lift gate 3A.

The sensor controlling section 33 controls a sensor section 112 (positioning sensor 113 and acceleration sensor 115) to acquire the sensor information. The information apparatus 110, which is always carried by the player, can acquire the same sensor information acquired by the sensor section 12 of the attachment device 10.

The communication processing section 35 controls a communication section 121 to cause it to transmit the sensor information to the server 50. The communication processing section 35 further accepts an interrupt process from the server 50 and activates the notification information processing section 137.

The notification information processing section 137, when it receives notification information, such as the going-off-course information, from the server 50, outputs the notification information to a notification section 116. The notification section 116, which includes a display section 118 and a sound output section 119, generates, for example, a display screen to be displayed on the display section 118 and voice data to be outputted to the sound output section 119 and outputs them to the display section 118 and the sound output section 119. The notification section 116 corresponds to the notification section set forth in the appended claims.

The notification information processing section 137 has the function of receiving display screen data having been transmitted from the server 50 to the display apparatus 7 and outputting the data to the display section 118. The display screen includes the analysis map screen, the density map screen, the analysis graph screen, and other types of screen. The screens formed of the screens D10, D20, and D30 can therefore be visually recognized on the display section 118. The display section 118 corresponds to the display apparatus attached to each of the players and the notification section that notifies the area situation information set forth in the appended claims.

The information apparatus 110 includes an operation section (not shown), and the player can operate the operation section to request the server 50 to transmit the analysis map screen, the density map screen, and the analysis graph screen. The player can visually recognize the screens when necessary.

As described above, the information notification system 101 according to the present embodiment can provide the following advantageous effects in addition to those provided by the first embodiment.

The player can visually recognize the area situation information, such as the analysis map screen, the density map screen, and the analysis graph screen, by looking at the display section 118 of the information apparatus 110 always carried by the player. The player can grasp the area situation information at an arbitrary location on the skiing ground and can therefore check the area situation information in the course of a sliding action and select a course suitable for the player's skill and sliding action method in the middle of practicing the sliding action on a course.

Further, since the information apparatus 110 may be an apparatus in the possession of the player, the player can use an apparatus that the player is accustomed to use everyday to purchase a lift ticket, pass through the automatic ticket examiner of the lift gate 3A, check the area situation information, and perform other types of operation. Use of the information apparatus 110 in the information notification system 101 allows a system highly convenient for the player to be provided.

Variations

An embodiment to which the invention is applicable is not limited to the embodiments described above, and the embodiments described above can be changed as appropriate to the extent that the change does not depart from the substance of the invention. Variations of the embodiments of the invention will be described below. In the following description, the same configurations as those in the embodiments described above have the same reference characters and will not be described in detail.

Variation 1

In the embodiments described above, the information notification systems 1 and 101 have been described with reference to the case where skiing is practiced on a skiing ground, but the present systems are not necessarily used on a skiing ground or in skiing and can be used in other winter sports, outdoor sports, and indoor sports.

For example, the present systems can also be used in a winter sport that is practiced on a fixed course (area), such as fun skiing, telemark skiing, snowboarding, airboarding, snow trekking using snowshoes, trekking, mountain biking, trail running, long trailing, rogaining, orienteering, and skiing and snowboarding on an indoor skiing ground.

Variation 2

In the embodiments and variation described above, the analysis map screen (screen D10) is a display screen showing information on players' positions, moving speeds, and moving directions on a planar conceptual map of the skiing ground, but not necessarily. For example, 3D video images of the players may be displayed on a 3D conceptual topographical map with the players' moving speeds and the moving directions conceptually displayed. Further, each of the regions displayed on the analysis map screen (regions A0 to A6, regions Z1 to Z3) may be displayed in the form of a figure or an illustration. Moreover, the averages and proportions of the moving speeds and the moving directions of the players displayed in the regions may be displayed in the form of a graph, an illustration, a symbol, a letter, an icon, or any other object on a region basis. Further, the moving speed may be expressed by using an animation.

Variation 3

The embodiments and variations described above have been described with reference to the case where the device attached to a player is the attachment device 10 or the information apparatus 110, and the device attached to a player may be a device having another form. For example, the device attached to a player can be a variety of information apparatus, such as a wristwatch-shaped electronic apparatus, an earphone-shaped electronic apparatus, a finger-ring-shaped electronic apparatus, a pendant-shaped electronic apparatus, an electronic apparatus attached to a sport gear or an outfit (goggles or gloves, for example) when used, a head mounted display (HMD), and a head-up display (HUD).

The entire disclosure of Japanese Patent Application No. 2016-065212, filed Mar. 29, 2016 is expressly incorporated by reference herein.

What is claimed is:

1. An information notification system comprising:
    at least one sensor attached to each player who is practicing an action in a target area; and
    a processor or integrated circuit configured to:
        acquire sensor data from the at least one sensor;
        generate area situation information on smoothness of movement of the players in the target area based on the sensor data acquired from the at least one sensor; and
        notifying the generated area situation information, wherein:
    the area situation information includes moving speeds of the players in the target area.

2. The information notification system according to claim 1, wherein the area situation information is screen information containing positions of the players or density of the players and the moving speeds displayed on a map of the target area.

3. The information notification system according to claim 2, wherein the target area is formed of a plurality of target areas, and the area situation information is screen information containing the density and the moving speeds diagrammatically expressed in each of the plurality of target areas.

4. The information notification system according to claim 1, wherein the processor or integrated circuit calculates trajectories along which the players practice the actions in the target area and a width of the target area where the players are allowed to practice the actions based on the sensor data.

5. The information notification system according to claim 4, wherein the processor or integrated circuit calculates a density of the players in the area based on the positions and the trajectories of the players in the target area and the width in the target area.

6. The information notification system according to claim 5, wherein the area situation information is screen information containing the density displayed on a map of the target area.

7. The information notification system according to claim 1, wherein
    the processor or integrated circuit generates going-off-course information when any of the players moves out of the area, and
    the processor or integrated circuit notifies the going-off-course information.

8. The information notification system according to claim 1, wherein each of the sensors includes a positioning sensor.

9. The information notification system according to claim 1, wherein the processor or integrated circuit notifies the generated area situation information via at least one of a display apparatus attached to each of the players, a display apparatus installed in the area, and a display apparatus provided in a server that acquires the sensor data from the sensors.

10. An information notification method comprising:
    acquiring sensor data from at least one sensor attached to each player who is practicing an action in a target area;
    generating area situation information on smoothness of movement of the players in the area based on the sensor data from the at least one sensor; and
    notifying the area situation information, wherein:
    the area situation information includes moving speeds of the players in the target area.

11. The information notification method according to claim 10, wherein the area situation information is screen information containing positions of the players or density of the players and the moving speeds displayed on a map of the target area.

12. The information notification method according to claim 11, wherein the target area is formed of a plurality of target areas, and the area situation information is screen information containing the density and the moving speeds diagrammatically expressed in each of the plurality of target areas.

13. The information notification method according to claim 10, wherein the generation of the area situation information includes calculating trajectories along which the players practice the actions in the target area and a width of an area where the players are allowed to practice the actions based on the sensor data.

14. The information notification method according to claim 13, wherein the generation of the area situation information includes calculating a density of the players in the area based on the positions and the trajectories of the players in the target area and the width in the target area.

15. The information notification method according to claim 14, wherein the area situation information is screen information containing the density displayed on a map of the target area.

16. The information notification method according to claim 10, wherein
the generation of the area situation information includes generating going-off-course information when any of the players moves out of the target area, and
the notification of the area situation information includes notifying the going-off-course information.

17. The information notification method according to claim 10, wherein each of the sensors includes a positioning sensor.

18. The information notification method according to claim 10, wherein the notification of the area situation information includes notifying the area situation information to at least one of a display apparatus attached to each of the players, a display apparatus installed in the area, and a display apparatus provided in a server that acquires the sensor data from the sensors.

19. A display apparatus for use with at least one player, the display apparatus comprising:
a display;
at least one sensor attached to each player who is practicing actions in a target area; and
a processor or integrated circuit configured to:
determine area situation information, via the at least one sensor, including a smoothness of movement of each player in the target area, and
display the area situation information on the smoothness of movement of each player in the target area, wherein:
the area situation information includes moving speeds of each player in the target area.

20. The display apparatus according to claim 19, wherein the area situation information is screen information containing positions of the players or density of the players and the moving speeds displayed on a map of the target area.

21. The display apparatus according to claim 20, wherein the target area is formed of a plurality of target areas, and the area situation information is screen information containing the density and the moving speeds diagrammatically expressed in each of the plurality of target areas.

22. The display apparatus according to claim 19, wherein sensor data from the at least one sensor is used to display trajectories along which the players practice the actions in the area and a width of an area where the players are allowed to practice the actions.

23. The display apparatus according to claim 22, wherein a density of the players in the area is displayed based on the positions and the trajectories of the players in the target area and the width in the target area.

24. The display apparatus according to claim 23, wherein the area situation information is screen information containing the density displayed on a map of the target area.

* * * * *